US010096977B2

(12) United States Patent
Nishida et al.

(10) Patent No.: US 10,096,977 B2
(45) Date of Patent: Oct. 9, 2018

(54) ION GENERATION APPARATUS AND ELECTRICAL EQUIPMENT

(71) Applicant: Sharp Kabushiki Kaisha, Osaka-shi, Osaka (JP)

(72) Inventors: Hiromu Nishida, Osaka (JP); Koichi Izu, Osaka (JP); Nobuyuki Ohe, Osaka (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 273 days.

(21) Appl. No.: 14/914,276

(22) PCT Filed: Aug. 26, 2014

(86) PCT No.: PCT/JP2014/072220
§ 371 (c)(1),
(2) Date: Feb. 25, 2016

(87) PCT Pub. No.: WO2015/049933
PCT Pub. Date: Apr. 9, 2015

(65) Prior Publication Data
US 2016/0218490 A1    Jul. 28, 2016

(30) Foreign Application Priority Data
Oct. 2, 2013    (JP) .................................. 2013-207389

(51) Int. Cl.
*H01T 23/00*    (2006.01)
*A61L 9/22*    (2006.01)
(Continued)

(52) U.S. Cl.
CPC ................ *H01T 23/00* (2013.01); *A61L 9/22* (2013.01); *H01T 19/04* (2013.01); *B03C 3/38* (2013.01); *B60H 3/0071* (2013.01); *F24F 3/166* (2013.01)

(58) Field of Classification Search
USPC .................................................. 361/230, 231
See application file for complete search history.

(56) References Cited

U.S. PATENT DOCUMENTS

2011/0000251 A1*   1/2011   Oka ....................... F24F 1/0011
                                                         62/404
2011/0085276 A1    4/2011   Nishida
(Continued)

FOREIGN PATENT DOCUMENTS

JP    2010-044917 A    2/2010
JP    2012-133999 A    7/2012
(Continued)

*Primary Examiner* — Danny Nguyen
(74) *Attorney, Agent, or Firm* — Keating & Bennett, LLP (57) ABSTRACT

In an ion generation apparatus, induction electrodes are formed on a surface of a substrate, holes are provided inside the induction electrodes, respectively, needle electrodes are disposed in a substrate, and tip end portions of the needle electrodes are inserted into the holes, respectively. Furthermore, a part of each of the induction electrodes is removed, thereby reducing the size of the substrate for entire size reduction. By such a configuration, it becomes possible to provide an ion generation apparatus that can stably generate ions even in a high humidity environment and that can be mounted also in small-sized electrical equipment.

5 Claims, 9 Drawing Sheets

(51) Int. Cl.
  *H01T 19/04* (2006.01)
  *B60H 3/00* (2006.01)
  *B03C 3/38* (2006.01)
  *F24F 3/16* (2006.01)

(56) References Cited

U.S. PATENT DOCUMENTS

2011/0102963 A1* 5/2011 Sekoguchi ................ A61L 9/22
                                                    361/230
2012/0068082 A1* 3/2012 Noda ...................... H01T 23/00
                                                    250/423 R
2014/0077701 A1  3/2014 Nishida
2014/0103793 A1  4/2014 Nishida et al.

FOREIGN PATENT DOCUMENTS

| | | |
|---|---|---|
| JP | 2012-243504 A | 12/2012 |
| JP | 2013-041681 A | 2/2013 |
| JP | 2013-065537 A | 4/2013 |
| WO | 2012/035757 A1 | 3/2012 |

* cited by examiner

ION GENERATION APPARATUS AND ELECTRICAL EQUIPMENT

TECHNICAL FIELD

The present invention relates to an ion generation apparatus and electrical equipment made using the same, and particularly to an ion generation apparatus including an induction electrode and a needle electrode, and generating ions, and electrical equipment made using the ion generation apparatus.

BACKGROUND ART

The ion generation apparatus includes a substrate, an induction electrode, and a needle electrode. The induction electrode is formed in an annular shape and mounted on the substrate. The needle electrode has a base end portion disposed in the substrate and a tip end portion arranged in the center portion of the induction electrode. When a high voltage is applied between the needle electrode and the induction electrode, corona discharge occurs at the tip end portion of the needle electrode, so that ions are generated. The generated ions are delivered by an air blower into a room, and then, surround fungi, bacteria and viruses floating in the air and degrade them (for example, see Japanese Patent Laying-Open No. 2010-044917 (PTD 1)).

CITATION LIST

Patent Document

PTD 1: Japanese Patent Laying-Open No. 2010-044917

SUMMARY OF INVENTION

Technical Problem

In the conventional ion generation apparatus, however, the needle electrode and the induction electrode are mounted on the surface of one substrate. Accordingly, when the ion generation apparatus is placed in a high humidity environment in the state where dust accumulates on the surface of the substrate, a current leaks between the needle electrode and the induction electrode through the dust absorbing moisture, so that the amount of ions to be generated may decrease.

Furthermore, since the induction electrode is formed of a plate-shaped metal, size reduction of this induction electrode becomes difficult, so that the entire ion generation apparatus cannot be reduced in size. Accordingly, it is difficult to mount an ion generation apparatus in portable small-sized electrical equipment.

Therefore, a main object of the present invention is to provide: an ion generation apparatus that can generate ions stably even in a high humidity environment, and can be mounted also in small-sized electrical equipment; and electrical equipment made using the ion generation apparatus.

Solution to Problem

An ion generation apparatus according to the present invention includes an induction electrode and a needle electrode, and generates ions. The ion generation apparatus includes: a first substrate provided with a hole; and a second substrate provided so as to face a surface of the first substrate on one side. The induction electrode is provided around the hole of the first substrate. The needle electrode has a base end portion disposed in the second substrate and a tip end portion inserted into the hole. Thus, the induction electrode and the needle electrode are separately provided in the first substrate and the second substrate, respectively. Accordingly, even when the ion generation apparatus is placed in a high humidity environment in the state where dust accumulates on each of these first and second substrates, a current can be prevented from leaking between the needle electrode and the induction electrode, so that ions can be stably generated.

Furthermore, a part of the induction electrode is removed in order to further allow size reduction of the entire ion generation apparatus, thereby reducing the size of the first substrate as small as possible, so that the entire ion generation apparatus is reduced in size.

Furthermore, since the first substrate and the second substrate are covered by insulating resin, dust can be prevented from accumulating on the first substrate and the second substrate. Furthermore, a current can be more effectively prevented from leaking between the needle electrode and the induction electrode.

Furthermore, the tip end portion of the needle electrode protrudes from the insulating resin. In this case, even when dust accumulates around the needle electrode, discharge of the needle electrode can be prevented from being blocked by the tip end portion of the needle electrode becoming buried in dust. Furthermore, even in the case where dust adheres to the tip end portion of the needle electrode, dust can be blown away from the needle electrode by applying a high voltage to the needle electrode while sending air to the tip end portion of the needle electrode.

Further preferably, based on a basic shape annularly formed around the hole of the first substrate, the induction electrode is formed such that a part of the basic shape is removed.

Further preferably, the first substrate is a printed circuit board, and the induction electrode is formed by a wiring layer of the printed circuit board. In this case, the induction electrode can be formed at low cost, so that the ion generation apparatus can be implemented at low cost.

Furthermore, electrical equipment according to the present invention includes: the above-described ion generation apparatus; and an air blowing unit for sending out ions generated in the ion generation apparatus.

Advantageous Effects of Invention

In the ion generation apparatus according to the present invention, the induction electrode and the needle electrode are separately provided in the first substrate and the second substrate, respectively. Accordingly, even when the ion generation apparatus is placed in a high humidity environment in the state where dust accumulates on each of the first and second substrates, a current can be prevented from leaking between the needle electrode and the induction electrode, so that ions can be stably generated.

DESCRIPTION OF EMBODIMENTS

First Embodiment

An ion generation apparatus according to one embodiment of the present invention includes: a needle electrode 1 for generating positive ions; a needle electrode 2 for generating negative ions; an annular induction electrode 3 for forming an electric field between this induction electrode 3 and needle electrode 1; an annular induction electrode 4 for forming an electric field between this induction electrode 4 and needle electrode 2; and two substrates 5 and 6 each formed in a rectangular shape, as shown in FIGS. 1 to 6.

Figure 1:
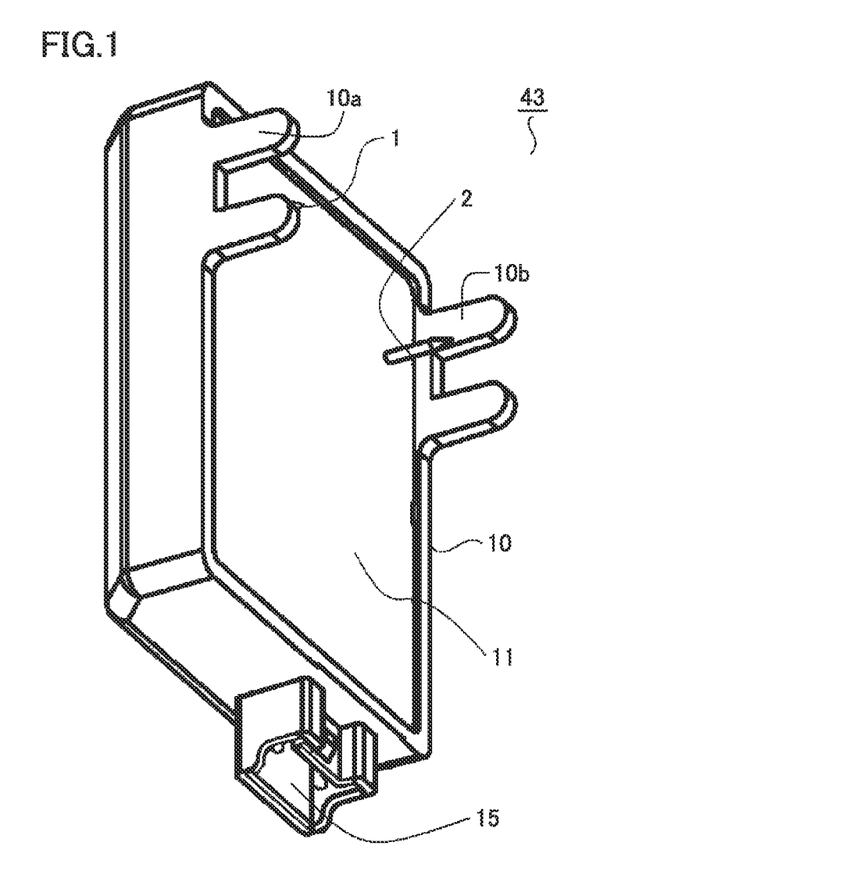
FIG. 1 is a perspective view showing an external appearance of an ion generation apparatus according to one embodiment of the present invention.
Figure 2:
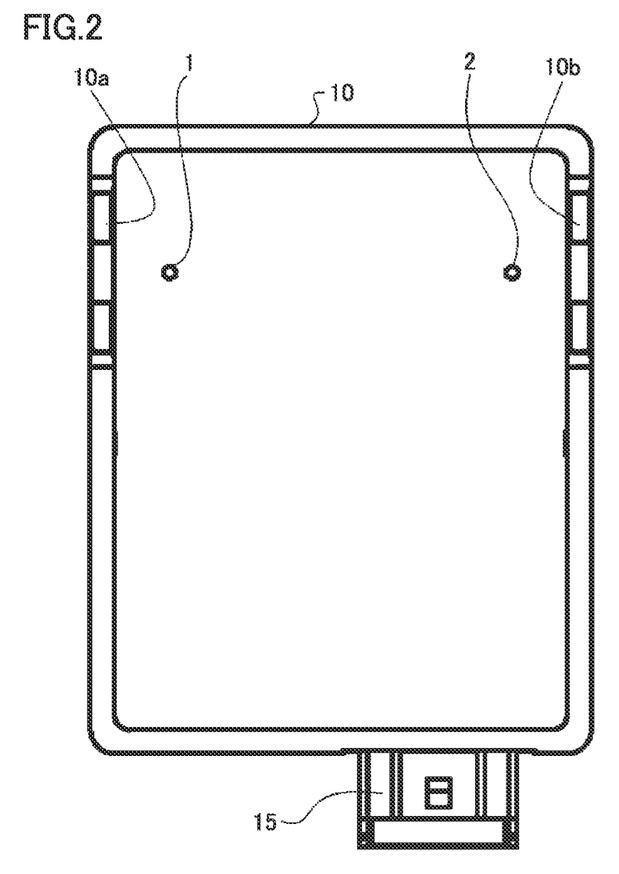
FIG. 2 is a plan view showing the external appearance of the ion generation apparatus shown in FIG. 1.
Figure 3:
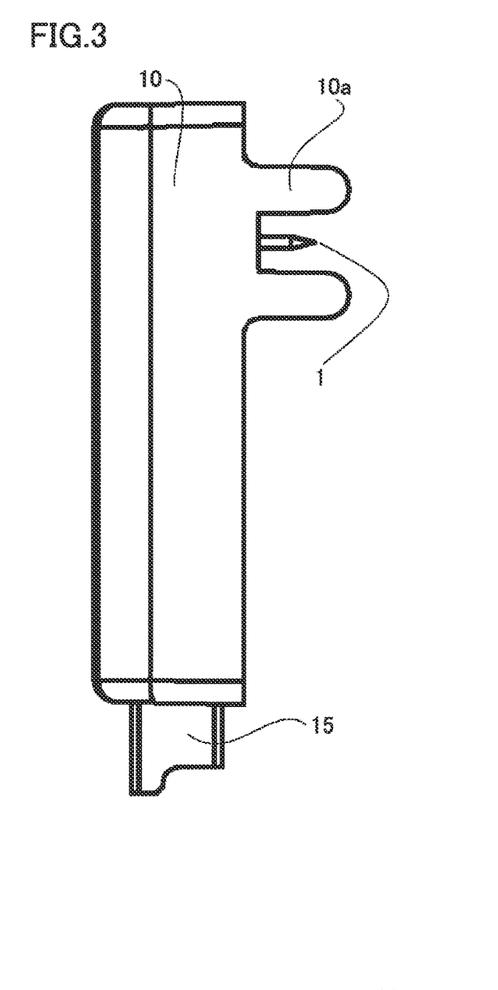
FIG. 3 is a side view showing the external appearance of the ion generation apparatus shown in FIG. 1.
Figure 4:
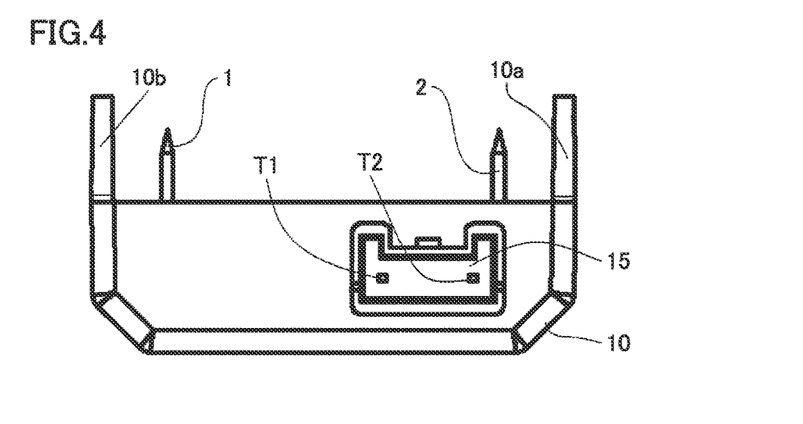
FIG. 4 is a bottom view showing the external appearance of the ion generation apparatus shown in FIG. 1.
Figure 5:
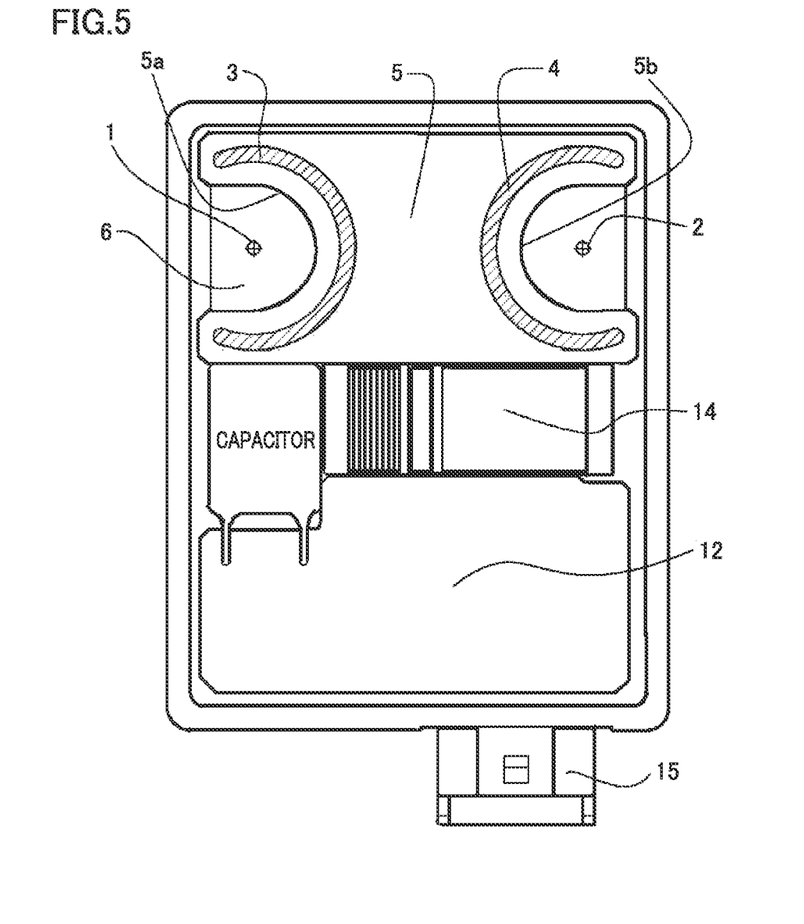
FIG. 5 is an internal structure diagram showing the state where insulating resin is removed from the ion generation apparatus shown in FIG. 2.
Figure 6:
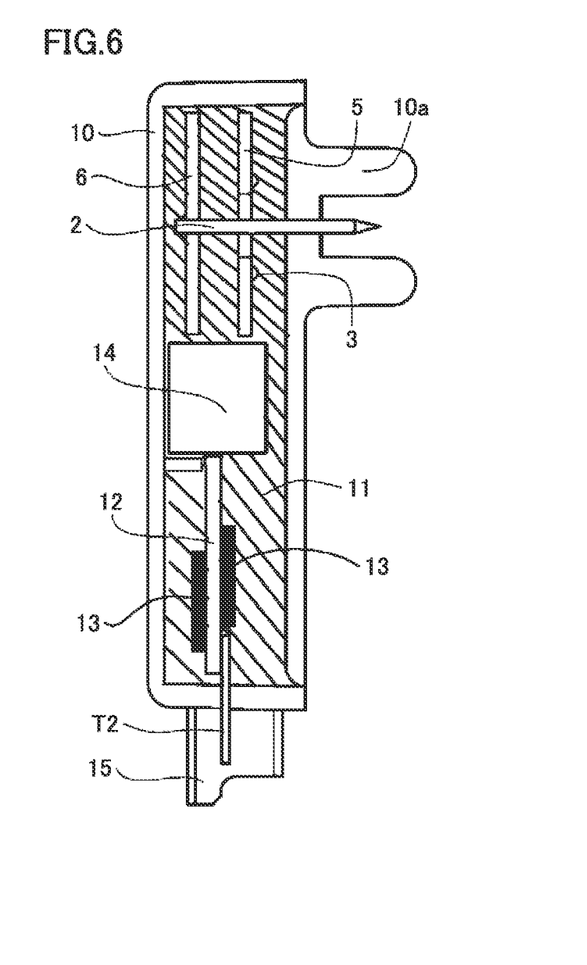
FIG. 6 is a cross-sectional view showing the internal structure of the ion generation apparatus shown in FIG. 3.

Substrates 5 and 6 are arranged at a prescribed distance in parallel with each other on the upper and lower sides as seen in FIG. 1. Induction electrode 3 is formed on the surface at one end of substrate 5 in the longitudinal direction using a wiring layer of substrate 5. Induction electrode 3 is provided inside with a hole 5a passing through substrate 5. Furthermore, induction electrode 4 is formed on the surface at the other end of substrate 5 in the longitudinal direction using a wiring layer of substrate 5. Induction electrode 4 is provided inside with a hole 5b passing through substrate 5. A part of each of induction electrodes 3 and 4 located on both outer sides, respectively, of substrate 5 is removed.

Each of needle electrodes 1 and 2 is arranged at a right angle to substrates 5 and 6. In other words, needle electrode 1 has: a base end portion that is inserted and fitted into the hole of substrate 6; and a tip end portion that passes through the center of hole 5a in substrate 5. Furthermore, needle electrode 2 has: a base end portion that is inserted and fitted into the hole of substrate 6; and a tip end portion that passes through the center of hole 5b in substrate 5. The base end portion of each of needle electrodes 1 and 2 is fixed to substrate 5 with solder. The tip end portion of each of needle electrodes 1 and 2 is keenly sharpened.

Furthermore, this ion generation apparatus includes: a housing 10 formed in a rectangular parallelepiped shape and having a rectangular opening slightly larger than substrates 5 and 6; insulating resin 11 for closing the opening in housing 10; a circuit substrate 12; a circuit component 13; and a transformer 14.

Housing 10 is formed by insulating resin. The lower portion of housing 10 is formed slightly smaller than the upper portion thereof and shaped like a bottom of a ship. Transformer 14 is housed inside housing 10 on one side of both substrate 5 and substrate 6. Circuit substrate 12 is provided across transformer 14 from substrate 5 and substrate 6. Circuit component 13 is mounted on circuit substrate 12.

Substrates 5 and 6 are housed on one end side of housing 10. On the other end side of housing 10, a connector 15 for feeding electric power is provided so as to protrude to the outside. Connector 15, circuit substrate 12, transformer 14, and substrates 5 and 6 are electrically connected by wiring. A high voltage portion within housing 10 is filled with insulating resin 11. Substrate 6 is filled to its lower surface with insulating resin 11. In the present embodiment, although circuit component 13 connected to the primary side of transformer 14 does not have to be insulated by insulating resin 11, the space within the housing is filled up with insulating resin 11 for reasons of operation.

While insulating resin 11 is applied so as to cover the outer surface of substrate 5, the tip end portions of needle electrodes 1 and 2 protrude above insulating resin 11 by 5 mm. Although the length of each of needle electrodes 1 and 2 protruding from insulating resin 11 is not particularly limited, an appropriate length is determined based on the voltage of high voltage electricity applied to the needle electrode and the amount of generated ions.

Figure 7:
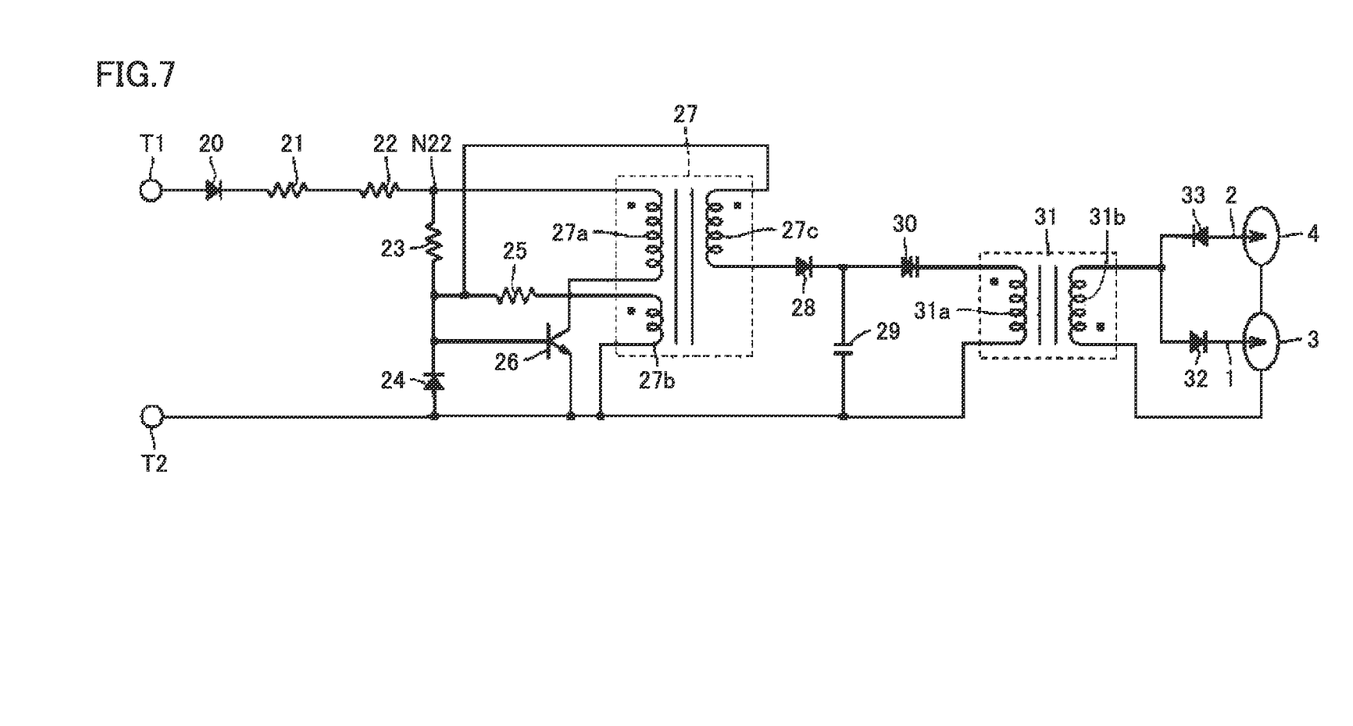
FIG. 7 is a circuit diagram showing the configuration of the ion generation apparatus in the embodiment of the present invention.

FIG. 7 is a circuit diagram showing the configuration of the ion generation apparatus. In FIG. 7, in addition to needle electrodes 1, 2 and induction electrodes 3, 4, the ion generation apparatus includes a power supply terminal T1, a grounding terminal T2, diodes 20, 24, 28, 32, and 33, resistance elements 21 to 23 and 25, an NPN bipolar transistor 26, boost transformers 27 and 31, a capacitor 29, and a 2-terminal thyristor 30. A portion of the circuit shown in FIG. 7 other than needle electrodes 1 and 2 and induction electrodes 3 and 4 is formed of circuit substrate 12, circuit component 13, transformer 14, and the like in FIG. 3.

The positive electrode and the negative electrode of a direct-current (DC) power supply are connected to power supply terminal T1 and grounding terminal T2, respectively. Power supply terminal T1 is applied with a DC power supply voltage (for example, +12V or +15V) while grounding terminal T2 is grounded. Diode 20 and resistance elements 21 to 23 are connected in series between power supply terminal T1 and the base of transistor 26. Transistor 26 has an emitter connected to grounding terminal T2. Diode 24 is connected between grounding terminal T2 and the base of transistor 26.

Diode 20 serves as an element for protecting a DC power supply by interrupting a current in the case where the positive electrode and the negative electrode of the DC power supply are inversely connected to terminals T1 and T2, respectively. Resistance elements 21 and 22 each serve as an element for limiting a voltage boosting operation. Resistance element 23 is a starting resistance element. Diode 24 operates as a reverse withstand voltage protection element for transistor 26.

Boost transformer 27 includes a primary winding 27a, a base winding 27b, and a secondary winding 27c. Primary winding 27a has one terminal connected to a node N22 between resistance elements 22 and 23, and the other terminal connected to the collector of transistor 26. Base winding 27b has one terminal connected to the base of transistor 26 through resistance element 25, and the other terminal connected to grounding terminal T2. Secondary winding 27c has one terminal connected to the base of transistor 26, and the other terminal connected to grounding terminal T2 through diode 28 and capacitor 29.

Boost transformer 31 includes a primary winding 31a and a secondary winding 31b. The 2-terminal thyristor 30 is connected between the cathode of diode 28 and one terminal of primary winding 31a. Primary winding 31a has the other terminal connected to grounding terminal T2. Secondary winding 31b has one terminal connected to induction electrodes 3 and 4, and the other terminal connected to the anode of diode 32 and the cathode of diode 33. The cathode of diode 32 is connected to the base end portion of needle electrode 1, and the anode of diode 33 is connected to the base end portion of needle electrode 2.

Resistance element 25 serves as an element for limiting a base current. The 2-terminal thyristor 30 serves as an element that is brought into a conductive state when the voltage between the terminals reaches a breakover voltage, and brought into a non-conductive state when the current is equal to or less than the minimum holding current.

Then, the operation of this ion generation apparatus will be hereinafter described. Capacitor 29 is charged by the RCC-type switching power supply operation. In other words, when a DC power supply voltage is applied between power supply terminal T1 and grounding terminal T2, a current flows from power supply terminal T1 through diode 20 and resistance elements 21 to 23 into the base of transistor 26, thereby bringing transistor 26 into a conductive state. Thereby, a current flows through primary winding 27a of boost transformer 27, and a voltage is generated between the terminals of base winding 27b.

The winding direction of base winding 27b is set so as to further raise the base voltage of transistor 26 when transistor 26 is brought into a conductive state. Accordingly, the voltage generated between the terminals of base winding 27b is in the positive feedback state, thereby lowering the conductive resistance value of transistor 26. At this time, the winding direction of secondary winding 27c is set such that current conduction is prevented by diode 28, so that a current is prevented from flowing through secondary winding 27c.

As the current flowing through primary winding 27a and transistor 26 continues to increase in this way, the collector voltage on transistor 26 rises beyond the saturation region. Thereby, the voltage between the terminals of primary winding 27a lowers and the voltage between the terminals of base winding 27b also lowers, while the collector voltage on transistor 26 further rises. Accordingly, the operation is carried out in the positive feedback state, to quickly bring transistor 26 into a non-conductive state. At this time, secondary winding 27c generates a voltage in the conductive direction of diode 28. Thereby, capacitor 29 is charged.

When the voltage between the terminals of capacitor 29 rises to reach the breakover voltage of 2-terminal thyristor 30, this 2-terminal thyristor 30 operates like a Zener diode to cause a current to further flow. When the current flowing through 2-terminal thyristor 30 reaches the breakover current, 2-terminal thyristor 30 is brought into an approximately short-circuited state. Then, the electric charge charged into capacitor 29 is discharged through 2-terminal thyristor 30 and primary winding 31a of boost transformer 31, so that an impulse voltage is generated in primary winding 31a.

When an impulse voltage is generated in primary winding 31a, a positive high voltage pulse and a negative high voltage pulse are alternately generated in secondary winding 31b while attenuating. The positive high voltage pulse is applied to needle electrode 1 through diode 32 while the negative high voltage pulse is applied to needle electrode 2 through diode 33. Thereby, a corona discharge occurs at the tip end of each of needle electrodes 1 and 2, thereby generating positive ions and negative ions, respectively.

On the other hand, when a current flows through secondary winding 27c of boost transformer 27, the voltage between the terminals of primary winding 27a rises to bring transistor 26 into a conductive state again. Then, the above-described operation is repeated. The rate of repeating this operation is increased as the current flowing through the base of transistor 26 is larger. Therefore, by adjusting the resistance value of resistance element 21, the current flowing through the base of transistor 26 is adjusted, so that the number of times of discharging needle electrodes 1 and 2 can be adjusted.

In the present embodiment, a positive high voltage electricity is caused to be applied to needle electrode 1 and a negative high voltage electricity is caused to be applied to needle electrode 2, so that positive ions are generated from needle electrode 1 and negative ions are generated from needle electrode 2.

In the present embodiment, a high voltage applied to each of needle electrodes 1 and 2 is adjusted, so that specific ions are generated. In this case, a positive ion is a cluster ion formed by a plurality of water molecules attached around a hydrogen ion ($H^+$) and represented by $H^+(H_2O)m$ (where m is an optional natural number). Furthermore, a negative ion is a cluster ion formed by a plurality of water molecules attached around an oxygen ion ($O_2^-$) and represented by $O_2^-(H_2O)n$ (where n is an optional natural number).

When positive ions and negative ions are emitted into a room, both ions surround fungi, bacteria and viruses floating in the air, and are attached and coupled to their surfaces, to cause a chemical reaction. Floating fungi, bacteria and the like are killed by sterilization due to actions of hydroxyl radicals (.OH) and hydrogen peroxide $H_2O_2$ that are active species and generated in this case.

Figure 8:
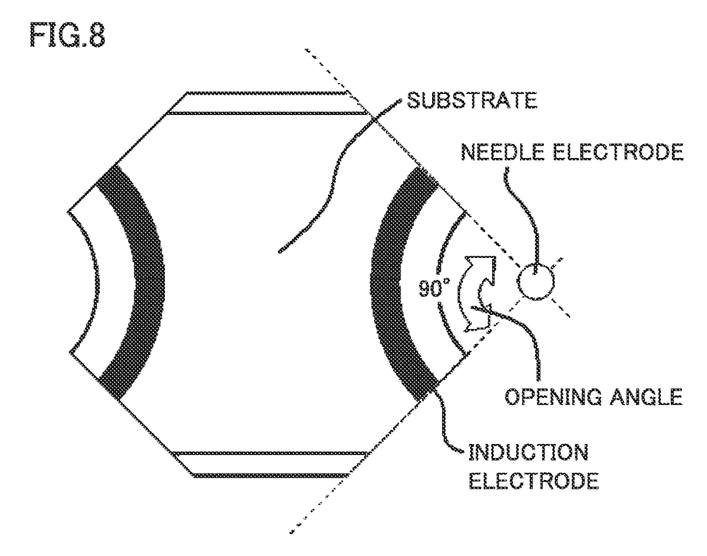
FIG. 8 is a diagram showing a method of forming an induction electrode of the ion generation apparatus in the embodiment of the present invention.

In the present embodiment, a part of induction electrode 3 and a part of induction electrode 4 are removed. A part of substrate 5 is also removed. Consequently, the size of substrate 5 in the longitudinal direction is reduced. FIG. 8 shows a definition of the shape of the induction electrode. The induction electrode is formed in a circular shape centering on the needle electrode, and a part of the induction electrode is removed so as to be formed in a sector shape centering on the needle electrode. FIG. 8 illustrates a shape represented based on the opening angle that is formed centering on the needle electrode between both ends of the remaining portion obtained by removing a part of the induction electrode. If the opening angle is 0° (degree), the entire induction electrode is removed. If the opening angle is 360° (degree), a complete ring is to be formed. In addition, it is preferable that the opening angle is horizontally symmetrical with respect to the needle electrode, but can be changed in a range in which the balance is not significantly changed.

Figure 9:
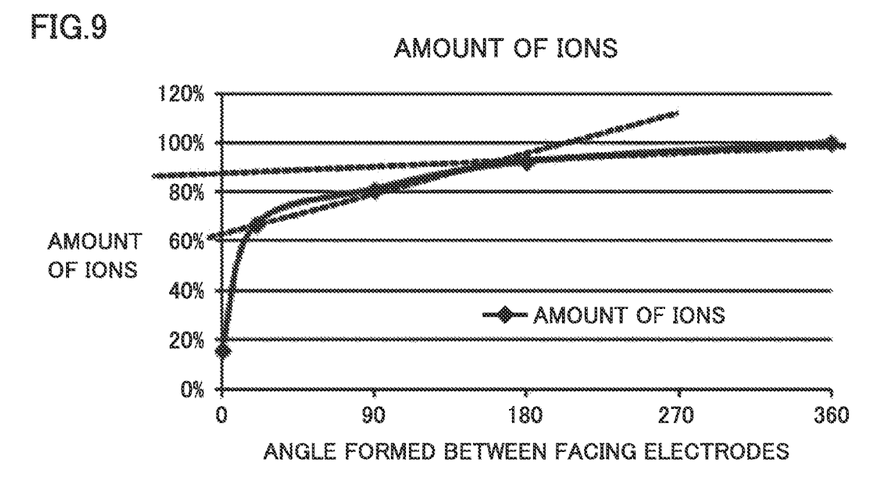
FIG. 9 is a diagram showing the relation between the shape of the induction electrode and the generated amount of ions regarding the ion generation apparatus in the embodiment of the present invention.
Figure 10A:
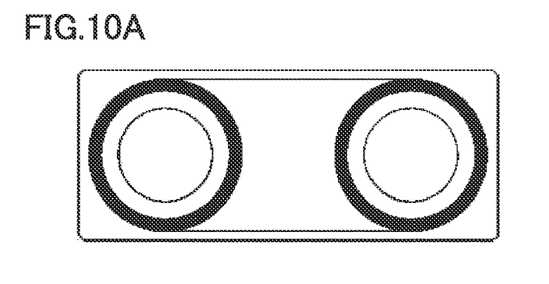
FIG. 10A is a diagram showing a prototype shape of the induction electrode of the ion generation apparatus in the embodiment of the present invention.
Figure 10B:
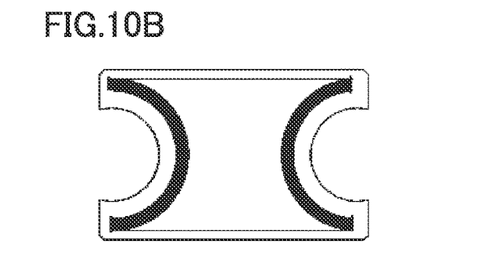
FIG. 10B is another diagram showing the prototype shape of the induction electrode of the ion generation apparatus in the embodiment of the present invention.
Figure 10C:
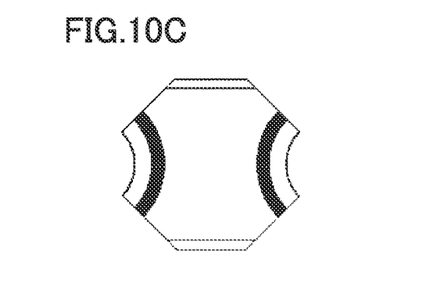
FIG. 10C is still another diagram showing the prototype shape of the induction electrode of the ion generation apparatus in the embodiment of the present invention.
Figure 10D:
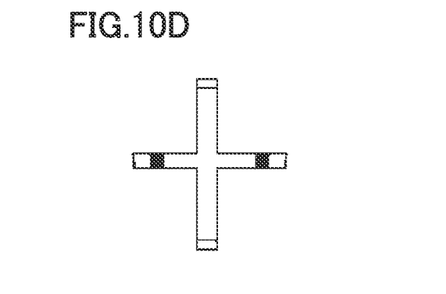
FIG. 10D is still another diagram showing the prototype shape of the induction electrode of the ion generation apparatus in the embodiment of the present invention.

FIG. 9 shows the relation between the opening angle of the induction electrode formed in a sector shape and the amount of generated ions. In the case where the opening angle is 20°, the amount of generated ions is about 65% of the amount of ions generated at the time when the opening angle is 360°. In the case where the opening angle is 90°, the amount of generated ions is about 80%. Also, in the case where the opening angle is 180°, the amount of generated ions is about 90%. Based on these results, the opening angle can be set at 20° or more and 360° or less, further more preferably 90° or more and 360° or less, and most preferably 180° or more and 360° or less.

FIG. 10 shows a prototype of an induction electrode. FIG. 10A shows a prototype shape of the induction electrode at the time when the opening angle is 360°. FIG. 10B shows a prototype shape of the induction electrode at the time when the opening angle is 180°. FIG. 10C shows a prototype shape of the induction electrode at the time when the opening angle is 90°. FIG. 10D shows a prototype shape of the induction electrode at the time when the opening angle is 20°.

Figure 11:
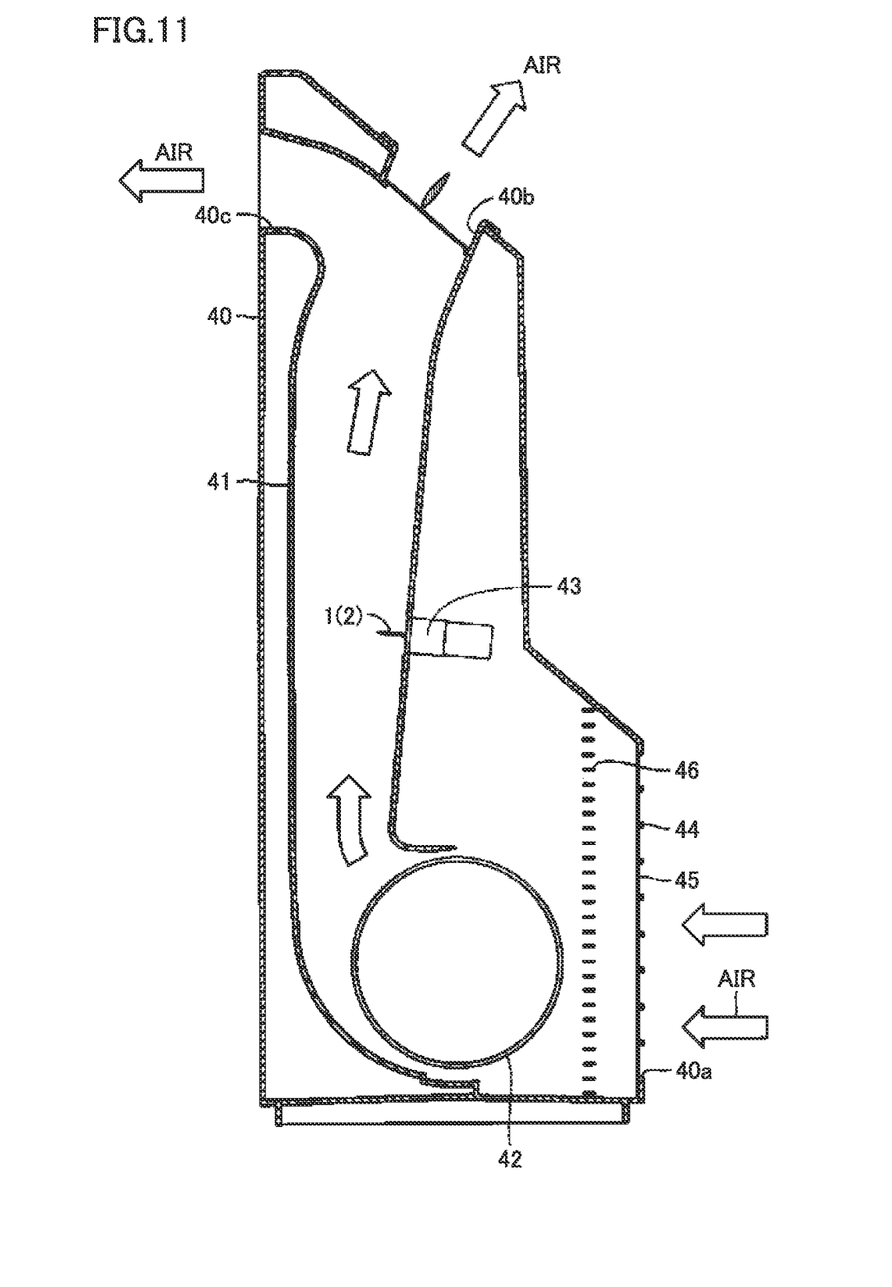
FIG. 11 is a cross-sectional view showing the configuration of an air cleaner made using the ion generation apparatus shown in FIG. 1.

FIG. 11 is a cross-sectional view showing the configuration of an air cleaner made using the ion generation apparatus shown in FIG. 1. In FIG. 11, in this air cleaner, an inlet port 40a is provided in the rear surface at the lower portion of main body 40, and outlet ports 40b and 40c are provided in the rear surface and front surface, respectively, in the upper portion of main body 40. Furthermore, duct 41 is provided inside main body 40. The opening at the lower end of duct 41 is provided so as to face inlet port 40a. The upper end of duct 41 is connected to outlet ports 40b and 40c.

A cross flow fan 42 is provided in the opening at the lower end of duct 41, and an ion generation apparatus 43 is provided in the center portion of duct 41. Ion generation apparatus 43 is the same as that shown in FIG. 1. The main body of ion generation apparatus 43 is fixed to the outer wall surface of duct 41, and needle electrodes 1 and 2 thereof penetrates through the wall of duct 41 and protrude into duct 41. Two needle electrodes 1 and 2 are arranged in the direction that is orthogonal to the direction in which the air flows through duct 41.

Furthermore, inlet port 40a is provided with a lattice-shaped grill 44 made of resin, and a mesh-like thin filter 45 is affixed to the inside of grill 44. A fan guard 46 is provided on the inner side of filter 45 so as to prevent foreign substances and user's fingers from coming into cross flow fan 42.

When cross flow fan 42 is driven to rotate, the air inside the room is suctioned through inlet port 40a into duct 41. Fungi, bacteria the like contained in the suctioned air are killed by sterilization by the ions generated by ion generation apparatus 43. The clean air having passed through ion generation apparatus 43 is emitted through outlet ports 40b and 40c into the room.

In the present embodiment, induction electrodes 3 and 4 are mounted on substrate 5, and needle electrodes 1 and 2 are mounted on substrate 6. Accordingly, even when the ion generation apparatus is placed in a high humidity environment, a current can be prevented from leaking between needle electrodes 1, 2 and induction electrodes 3, 4, so that ions can be stably generated.

Furthermore, since substrates 5 and 6 are covered by insulating resin 11, dust can be prevented from accumulating on substrates 5 and 6.

Furthermore, the tip end portions of needle electrodes 1 and 2 protrude above insulating resin 11. Accordingly, even in the case where dust accumulates in the vicinity of the opening, discharge of needle electrodes 1 and 2 can be prevented from being blocked by the tip end portions of needle electrodes 1 and 2 becoming buried in dust. Furthermore, even in the case where dust adheres to the tip end portions of needle electrodes 1 and 2, dust can be blown away from needle electrodes 1 and 2 by applying a high voltage to needle electrodes 1 and 2 while sending air to the tip end portions of needle electrodes 1 and 2.

Furthermore, since induction electrodes 3 and 4 each are formed using a wiring layer of substrate 5, induction electrodes 3 and 4 can be formed at low cost, so that the ion generation apparatus can be implemented at low cost.

Second Embodiment

In the first embodiment, based on the basic shape formed in a circular shape, the induction electrode is formed by removing a part of the basic shape, but this basic shape can be treated functionally equally to a circular shape as long as this basic shape is polygonal equal to or greater than hexagonal. Also, even if the basic shape is triangular or rectangular, the basic shape can be implemented in a shape similar to that in the present embodiment depending on the arrangement manner. As an example of the arrangement manner, the induction electrodes may be arranged horizontally symmetrical with respect to the position of the needle electrode as an object axis, which is considered as being applicable to practical use in the same way.

Third Embodiment

In the first embodiment, the tip ends of needle electrodes 1 and 2 protrude above insulating resin 11, but the tip ends of needle electrodes 1 and 2 may be located lower than the upper surface of insulating resin 11.

Fourth Embodiment

In the first embodiment, each of induction electrodes 3 and 4 is formed using a wiring layer of substrate 5, but each of induction electrodes 3 and 4 may be formed of a metal plate. Furthermore, each of induction electrodes 3 and 4 may not be formed in an annular shape.

It should be understood that the embodiments disclosed herein are illustrative and non-restrictive in every respect. The scope of the present invention is defined by the terms of the claims, rather than the description above, and is intended to include any modifications within the meaning and scope equivalent to the terms of the claims.

REFERENCE SIGNS LIST 1, 2 needle electrode, 3, 4 induction electrode, 5, 6 substrate, 5a, 5b hole, 10 housing, 11 insulating resin, 12 circuit substrate, 13 circuit component, 14 transformer, 15 connector, T1 power supply terminal, T2 grounding terminal, 20, 24, 28, 32, 33 diode, 21 to 23, 25 resistance element, 26 NPN bipolar transistor, 27, 31 boost transformer, 27a, 31a primary winding, 27b base winding, 27c, 31b secondary winding, 29 capacitor, 30 2-terminal thyristor, 40 main body, 40a inlet port, 40b, 40c outlet port, 41 duct, 42 cross flow fan, 43 ion generation apparatus, 44 grill, 45 filter, 46 fan guard.

The invention claimed is:

1. An ion generation apparatus including an induction electrode and a needle electrode, and generating ions in air, the ion generation apparatus comprising:
a first substrate provided with a hole; and
a second substrate provided so as to face a surface of the first substrate on one side, wherein the induction electrode is provided around the hole of the first substrate and formed such that a part of a basic shape of the induction electrode is removed, the needle electrode includes a base end portion disposed in the second substrate and a tip end portion inserted into the hole, the basic shape of the induction electrode is formed so as to extend annularly around the hole of the first substrate, and a part of the basic shape and a part of the first substrate corresponding thereto are removed.

2. The ion generation apparatus according to claim 1, further comprising:

a housing that houses the first substrate and the second substrate and has one surface provided with an opening; and insulating resin that covers the first substrate and the second substrate, and seals the opening.

3. The ion generation apparatus according to claim 2, wherein the tip end portion of the needle electrode protrudes from the insulating resin.

4. The ion generation apparatus according to claim 1, wherein the first substrate is a printed circuit board, and the induction electrode is formed by a wiring layer of the printed circuit board.

5. Electrical equipment comprising:

the ion generation apparatus according to claim 1; and an air blowing unit for sending out ions generated in the ion generation apparatus.

* * * * *